United States Patent
Cohen et al.

(10) Patent No.: US 6,890,299 B2
(45) Date of Patent: May 10, 2005

(54) METHOD AND APPARATUS FOR MONITORING HEMOSTASIS IN CONNECTION WITH ARTIFICIAL SURFACE DEVICES

(75) Inventors: Eli Cohen, Skokie, IL (US); Irene Navickas, Northbrook, IL (US)

(73) Assignee: Haemoscope Corporation, Niles, IL (US)

( * ) Notice: Subject to any disclaimer, the term of this patent is extended or adjusted under 35 U.S.C. 154(b) by 114 days.

(21) Appl. No.: 10/409,479

(22) Filed: Apr. 8, 2003

(65) Prior Publication Data

US 2004/0203163 A1 Oct. 14, 2004

(51) Int. Cl.[7] .......................... A61B 5/00; G01N 33/86
(52) U.S. Cl. ................................. 600/369; 436/69
(58) Field of Search ..................... 600/368, 369, 600/300; 73/64.43; 436/69; 422/73

(56) References Cited

U.S. PATENT DOCUMENTS

| | | | |
|---|---|---|---|
| 5,167,145 A | | 12/1992 | Butler et al. |
| 5,646,046 A | * | 7/1997 | Fischer et al. ............... 436/49 |
| 6,060,323 A | | 5/2000 | Jina |
| 6,537,819 B2 | | 3/2003 | Cohen et al. |
| 6,541,262 B1 | * | 4/2003 | Baugh et al. ............... 436/69 |
| 6,613,573 B1 | | 9/2003 | Cohen |
| 6,787,363 B2 | * | 9/2004 | Cohen et al. ............... 436/69 |
| 2002/0178126 A1 | | 11/2002 | Beck et al. |
| 2002/0198740 A1 | | 12/2002 | Roman et al. |

FOREIGN PATENT DOCUMENTS

EP      0 525 273 A1      2/1991

OTHER PUBLICATIONS

Shore–Lesserson et al., Thromboelastography–Guided Transfusion Algorithm Reduces Transfusions in Complex Cardiac Surgery, Anesthesia and Analgesis (abstract), Feb. 1999, 1 page.

Frenette et al., Effectiveness of Conjugated Estrogen in Orthotopic Liver Transplantation, Southern Medical Journal, vol. 91, Apr. 1998, pp. 365–368.

Nguyen et al., A Web–Based Teaching Program for Laboratory Diagnosis of Coagulation Disorders, Arch. Pathol. Lab. Med., vol. 124, Apr. 2000, pp. 588–593.

International Search Report for Application No. PCT/US03/30710 dated Apr. 21, 2004.

* cited by examiner

Primary Examiner—Robert L. Nasser
Assistant Examiner—Navin Natnithithadha
(74) Attorney, Agent, or Firm—Marshall, Gerstein & Borun LLP

(57) ABSTRACT

A method and apparatus for monitoring hemostasis in a connection with a recipient of an artificial surface device provide a multi-phase monitoring protocol. In a first, pre- and intra-operative phase, hemostasis of the recipient is monitored relative to preventing clot formation to achieve artificial surface patency. In a second, post operative phase hemostasis of the recipient is monitored relative to bringing about clot formation to achieve vascular recovery. In a third, stabilizing intensive care phase hemostasis of the recipient is monitored relative to balancing hemostasis toward an anticoagulation bias. In a fourth, maintenance phase hemostasis is monitored relative to maintaining balanced hemostasis.

16 Claims, 8 Drawing Sheets

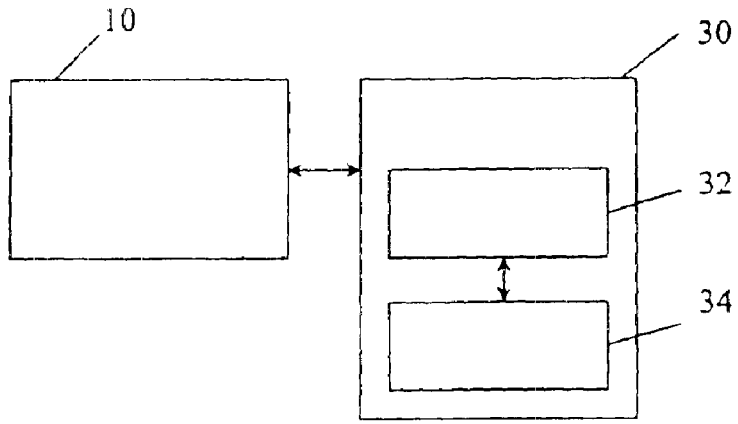

FIG. 4

III. Treatment Guide

| TEG® value | Hemostasis state | Common treatment |
|---|---|---|
| R between 11-14 min | ↓ clotting factors | x 2 FFP or 8 ml/kg[7,8,26] |
| R greater than 14 min | ↓↓ clotting factors | x 4 FFP or 16 ml/kg[1,5,26] |
| between 46-54 mm | ↓ platelet function | .3 µg/kg DDAVP[27,11] |
| between 41-45 mm | ↓↓ platelet function | x5 platelet units[8,26] |
| at 40 mm or less | ↓↓↓ platelet function | x10 platelet units[5,26,8,1] |
| α less than 45° | ↓ fibrinogen level | .06 u/kg cryo[5] |
| LY30 at 7.5% or greater, C.I. less than 1.0 | Primary fibrinolysis | antifibrinolytic of choice |
| LY30 at 7.5% or greater, C.I. greater than 3.0 | Secondary fibrinolysis | anticoagulant of choice |
| LY30 less than 7.5%, C.I. greater than 3.0 | Prothrombotic state | anticoagulant of choice |
| R less than 4 min or MA greater than 73 | Prothrombotic state | anticoagulant of choice |

FIG. 7

I. Sampling Protocol — All samples are Kaolin activated | If HIT, common treatment is with other thrombin-inhibitors such as Hirudin, Angiomax, etc., or a combination of platelet-inhibitor drugs with heparin.

/ 100

| Sample # | When | Cup type | Measures | If TEG® testing shows: | Common Treatment |
|---|---|---|---|---|---|
| 1 & 2 | On induction | Split sample:<br>• Heparinase bonded (blue) cup and pin<br>• Plain (clear) cup and pin<br><br>(If no heparin has been administered, place 5ul heparin (1,000 USP/cc) in each cup to test for ATIII deficiency.) | Baseline hemostasis profile | Prothrombotic state. AT III deficiency or others | • Treat with AT III or FFP<br>Antifibrinolytic drugs are contraindicated unless patient treated with Plavix, ReoPro, Aggrastat, or Integrilin, in which case Aprotinin is recommended |
| | | | | Evaluation for ATIII deficiency. When heparin has been administered to either the patient or sample cup : if Heparinase R and Plain R are the same, ATIII deficiency present | |
| 3 | At rewarming (approx 35°C) on CPB | Heparinase bonded (blue) cup and pin | Coagulopathy, if any, developed during bypass phase | Coagulopathy (see Decision Tree) | • Treat hyperfibrinolysis, according to Treatment Guide below.<br>Order blood product according to Treatment Guide below. |
| 4 & 5 | 10 min post protamine | Split sample:<br>• Heparinase bonded (blue) cup and pin<br>• Plain (clear) cup and pin | • Post-CPB hemostasis profile<br>• Heparin reversal | Heparinase R and Plain R are within normal limits, heparin is effectively reversed | None |
| | | | | Heparinase R normal, Plain R above normal limits, heparin is not completely reversed | Treat with Protamine |
| | | | | Coagulopathy (see Decision Tree) | See Treatment Guide below |
| 6 & 7 | Post op | Split sample:<br>• Heparinase bonded (blue) cup and pin<br>• Plain (clear) cup and pin | Post-op hemostasis profile♦ (see Notes section below) | Normal | None |
| | | | | Coagulopathy / heparin rebound see Decision Tree / see above @ 485 | See Treatment Guide below |

FIG. 5

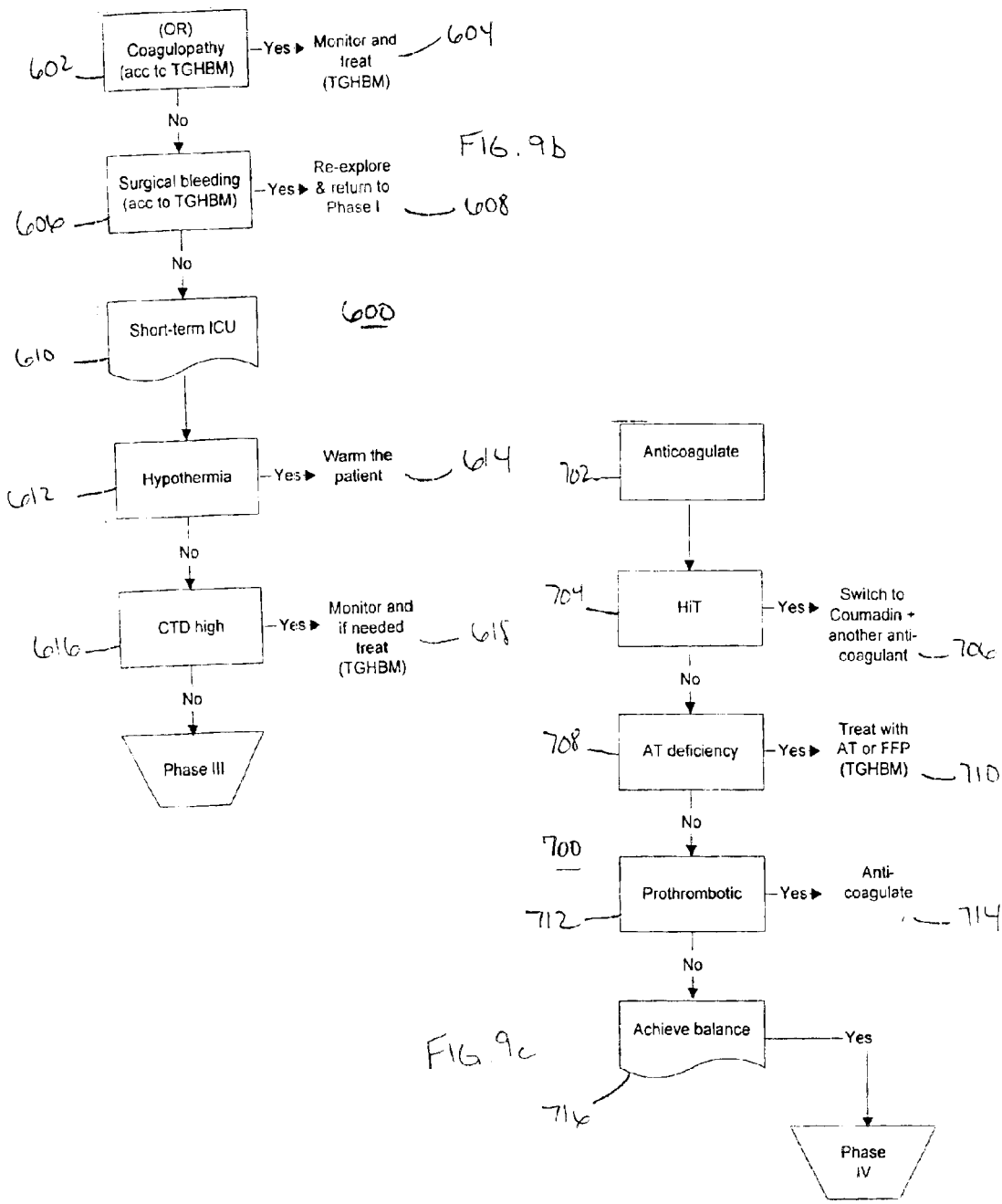

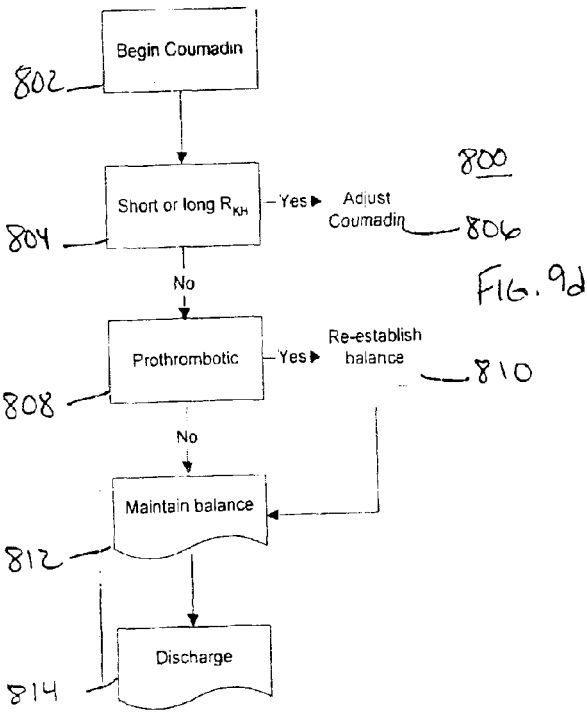

FIG. 9d

| Rationale | Test Result | Suggested Therapy | Target % inhibition* |
|---|---|---|---|
| Measure aspirin effect one hour after initial dose to determine whether the patient is resistant to aspirin and if aspirin therapy is sufficient | $MA_{KH}$ < 56mm | None | NA |
| | $MA_{KH}$ between 56 and 73 mm | Aspirin | 70-100** |
| | $MA_{KH}$ > 73mm | Aspirin plus Plavix | 70-100 ** (aspirin)*** 20-40 (Plavix)*** |
| In the presence of aspirin resistance | $MA_{KH}$ > 55mm | Plavix | 40 |
| In the presence of Plavix resistance | $MA_{KH}$ > 73mm | Aspirin | 100** |

* Target % inhibition is calculated based on $MA_{KH}$ compared to $MA_{Pi}$ for aspirin and $MA_{Pi}$ for Plavix
** 100% inhibition of thromboxane 2 receptors is permissible due to the presence of ADP agonist released by the activated platelets
*** Analysis of both aspirin and Plavix % inhibition should reach target levels, else consider Persantine, as described below Definitions:
$MA_{KH}$: TEG® MA using sample treated with both kaolin and heparinase
$MA_{Pi}$: TEG® MA using Platelet Inhibition assay for GPIIb/IIIa, ADP, or thromboxane A2 receptors (see Appendix D)

FIG. 10

METHOD AND APPARATUS FOR MONITORING HEMOSTASIS IN CONNECTION WITH ARTIFICIAL SURFACE DEVICES

TECHNICAL FIELD

This patent relates generally to the field of hemostasis, and more particularly, this patent relates to a method and apparatus of hemostasis, blood product and pharmaceutical management for recipients of artificial surface devices.

BACKGROUND

Blood is the circulating tissue of an organism that carries oxygen and nutritive materials to the tissues and removes carbon dioxide and various metabolic products for excretion. Whole blood consists of pale yellow or gray yellow fluid, plasma, in which are suspended red blood cells, white blood cells, platelets, and hemostatic factors.

An accurate measurement of the ability of a patient's blood to coagulate and lyse in a timely and effective fashion is crucial to certain surgical and medical procedures. Accelerated (rapid) and accurate detection of abnormal hemostasis is also of particular importance in respect of appropriate treatment to be given to patients suffering from coagulopathies and to whom it may be necessary to administer anticoagulants, antifibrinolytic agents, thrombolytic agents, anti-platelet agents, or blood components in a quantity which must clearly be determined after taking into account the abnormal components or "factors" of the patient's blood that may be contributing to the clotting disorder.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. The beginning of the coagulation process is the initial fibrin formation and platelet aggregation (FIG. 1a) and the end result of the coagulation process is a three-dimensional network of polymerized fibrin(ogen) fibers which together with platelet glycoprotein IIb/IIIa (GPIIb/IIIa) receptor bonding forms the final clot (FIG. 1b). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

Thus, the clot that develops and adheres to the damaged vascular system as a result of activated coagulation and resists the deforming shear stress of the circulating blood is, in essence, a mechanical device, formed to provide a "temporary stopper," which resists the shear force of circulating blood during vascular recovery. The kinetics, strength, and stability of the clot, that is, its physical property to resist the deforming shear force of the circulating blood, determine its capacity to do the work of hemostasis, which is to stop hemorrhage without permitting inappropriate thrombosis. This is exactly what the Thrombelastograph® (TEG®) hemostasis analysis system, described below, is designed to do, which is to measure the time it takes for initial fibrin formation, the time it takes for the clot to reach its maximum strength, the actual maximum strength, and the clot's stability.

Blood hemostasis analyzer instruments have been known since Professor Helmut Hartert developed such a device in Germany in the 1940's. One type of blood hemostasis analyzer is described in commonly assigned U.S. Pat. Nos. 5,223,227 and 6,225,126, the disclosures of which are hereby expressly incorporated herein by reference. This instrument, the TEG® hemostasis analysis system, monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood; in essence, the clot is the elementary machine of hemostasis, and the TEG® hemostasis analysis system measures the ability of the clot to perform mechanical work throughout its structural development. The TEG® hemostasis analysis system measures continuously all phases of patient hemostasis as a net product of whole blood components in a non-isolated, or static fashion from the time of test initiation until initial fibrin formation, through clot rate strengthening and ultimately clot strength through fibrin platelet bonding via platelet GPIIb/IIIa receptors and clot lysis.

The use of cardiac bypass, cardiac assist devices, cardiac replacement devices (artificial heart devices) and the like exposes blood to artificial surfaces and introduces flow turbulence. This almost invariably leads to the depositing of a layer of adherent and activated platelets, often with activation of the intrinsic and/or extrinsic system, resulting in the formation of thrombi. Gross thrombotic deposits may impede the function of the artificial organ, and thrombotic deposits may fragment and be swept downstream to distal organs potentially causing stroke, DVT, and other similar ailments. Thus, there is a need for a protocol for the clinical monitoring of artificial assist device (ASD) affected patient hemostasis to address the concerns of both thrombosis and hemorrhage.

BRIEF DESCRIPTION OF THE DRAWINGS

FIG. 4 is a block diagram illustrating an apparatus for the management of patient hemostasis and blood product or pharmaceutical therapy.

FIG. 5 is a table illustrating the sampling procedure for a hemostasis analyzer guided procedure for the management of patient hemostasis and blood therapy.

FIG. 7 is a table illustrating a treatment guide providing guidance and treatment suggestions based on hemostasis analysis results.

FIGS. 9a–9d are flow charts illustrating the phased monitoring protocol of FIG. 8 for ASD recipients.

FIG. 10 is a table illustrating an anticoagulation protocol.

DETAILED DESCRIPTION OF THE PREFERRED EMBODIMENTS

A procedure for hemostasis and blood management, particularly for artificial surface device (ASD) recipients, includes a monitoring and treatment protocol from pre-operative through discharge and long term hemostasis management. While described herein particularly in connection with ASD, the method and apparatus are generally applicable in any field using hemostasis analysis in the management of patient hemostasis, blood product usage and pharmaceutical therapy.

Figure 1A:
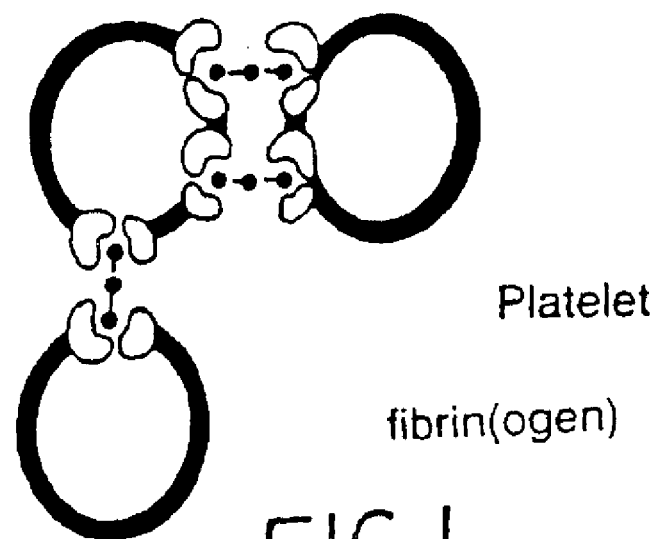
FIG. 1a is graphic illustration representing the mechanism of platelet aggregation.
Figure 1B:
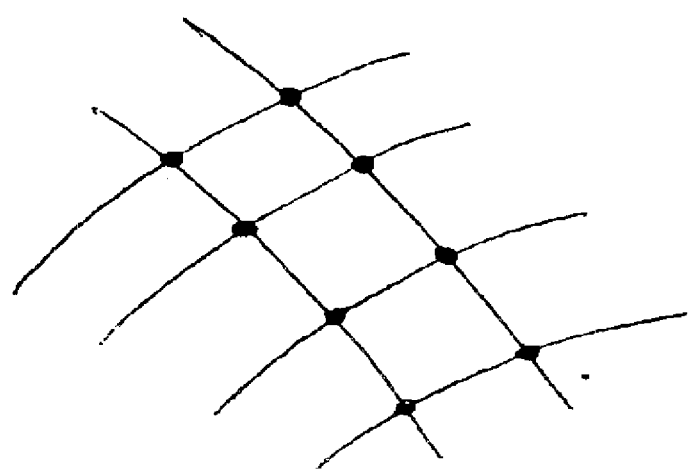
FIG. 1b is graphic illustration representing a fibrin/platelet network.
Figure 2:
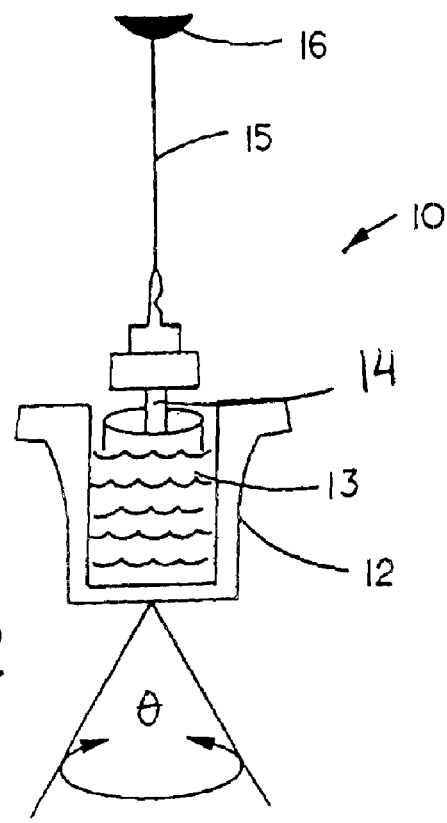
FIG. 2 is a schematic diagram of a blood coagulation analyzer in accordance with a preferred embodiment of the invention.

A procedure for management of hemostasis, blood product usage and pharmaceutical therapy according to an embodiment of the invention, utilizes a blood hemostasis analyzer 10, such as the Thrombelastograph® (TEG®) hemostasis analysis system referenced above, to measure the clot's physical properties. An exemplary blood hemostasis analyzer 10 is described in detail in U.S. Pat. No. 6,225,126, the disclosure of which is hereby expressly incorporated herein by reference, and a complete discussion is not repeated here. With reference to FIG. 2, to assist in the understanding of the procedure, however, a brief description of the blood hemostasis analyzer 10 is provided. The blood hemostasis analyzer uses a special cylindrical cup 12 that holds a blood sample 13. The cup 12 is coupled to a drive mechanism that causes the cup to oscillate through an angle θ, preferably about 4° 45'. Each rotation cycle lasts 10 seconds. A pin 14 is suspended in the blood sample 13 by a torsion wire 15, and the pin 14 is monitored for motion. The torque of the rotating cup 12 is transmitted to the immersed pin 14 only after fibrin-platelet bonding has linked the cup 12 and pin 14 together. The strength of these fibrin-platelet bonds affects the magnitude of the pin motion, such that strong clots move the pin 14 directly in phase with the cup motion. Thus, the magnitude of the output is directly related to the strength of the formed clot. As the clot retracts or lyses, these bonds are broken and the transfer of cup motion is diminished.

The rotation movement of the pin 14 is converted by a transducer 16 to an electrical signal, which can be monitored by a computer 30 (FIG. 4) including a processor 32 and a control program 34. The computer 30 is operable on the electrical signal to create a signature graph and a series of numeric parameters (collectively, hemostasis profile) corresponding to the measured clotting process. Additionally, the computer may include a visual display or be coupled to a printer (not depicted) to provide a visual representation of the hemostasis profile. Such a configuration of the computer is well within the skills of one having ordinary skill in the art, and while shown as a separate component may be integrated with the blood hemostasis analyzer.

Figure 3:
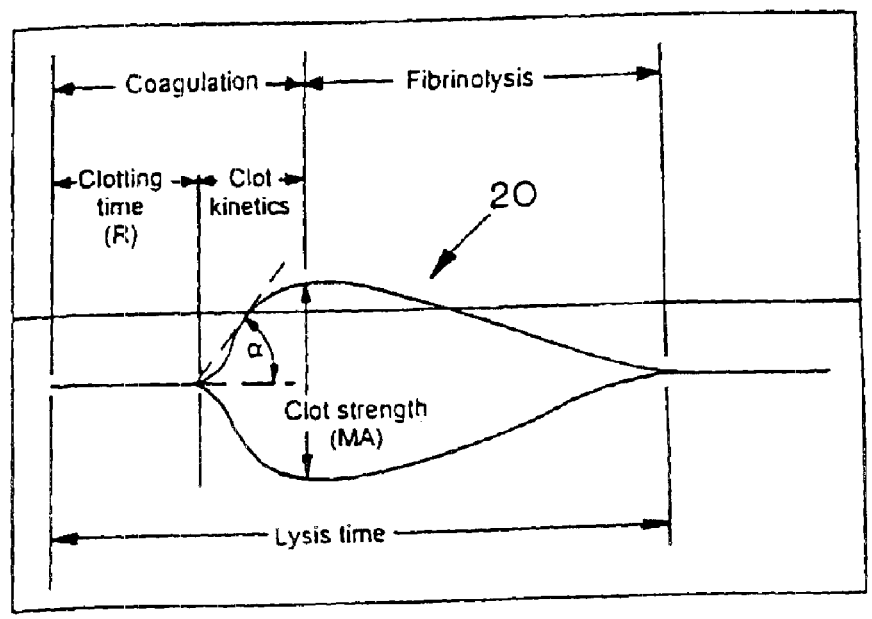
FIG. 3 is a plot illustrating a hemostasis profile generated by the blood coagulation analyzer shown in FIG. 2.

As shown in FIG. 3, the resulting hemostasis profile 20 is a measure of the time it takes for the first fibrin strand to be formed, the kinetics of clot formation, the strength of the clot and dissolution of the clot. Table I, below, provides definitions for several of these measured parameters.

TABLE I

| | |
|---|---|
| R | R time is the period of time of latency from the time that the blood was placed in the TEG ® hemostasis analyzer until the initial fibrin formation. |
| α | measures the rapidity of fibrin build-up and cross-linking (clot kinetics) |

TABLE I-continued

| | |
|---|---|
| MA | MA, or Maximum Amplitude, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents clot lysis. |

Of course, the procedure described herein may be adapted for use with hemostasis analysis machines that provide the above parameters, additional parameters or different parameters. Such machines are commercially available from various manufacturers.

Figure 6:
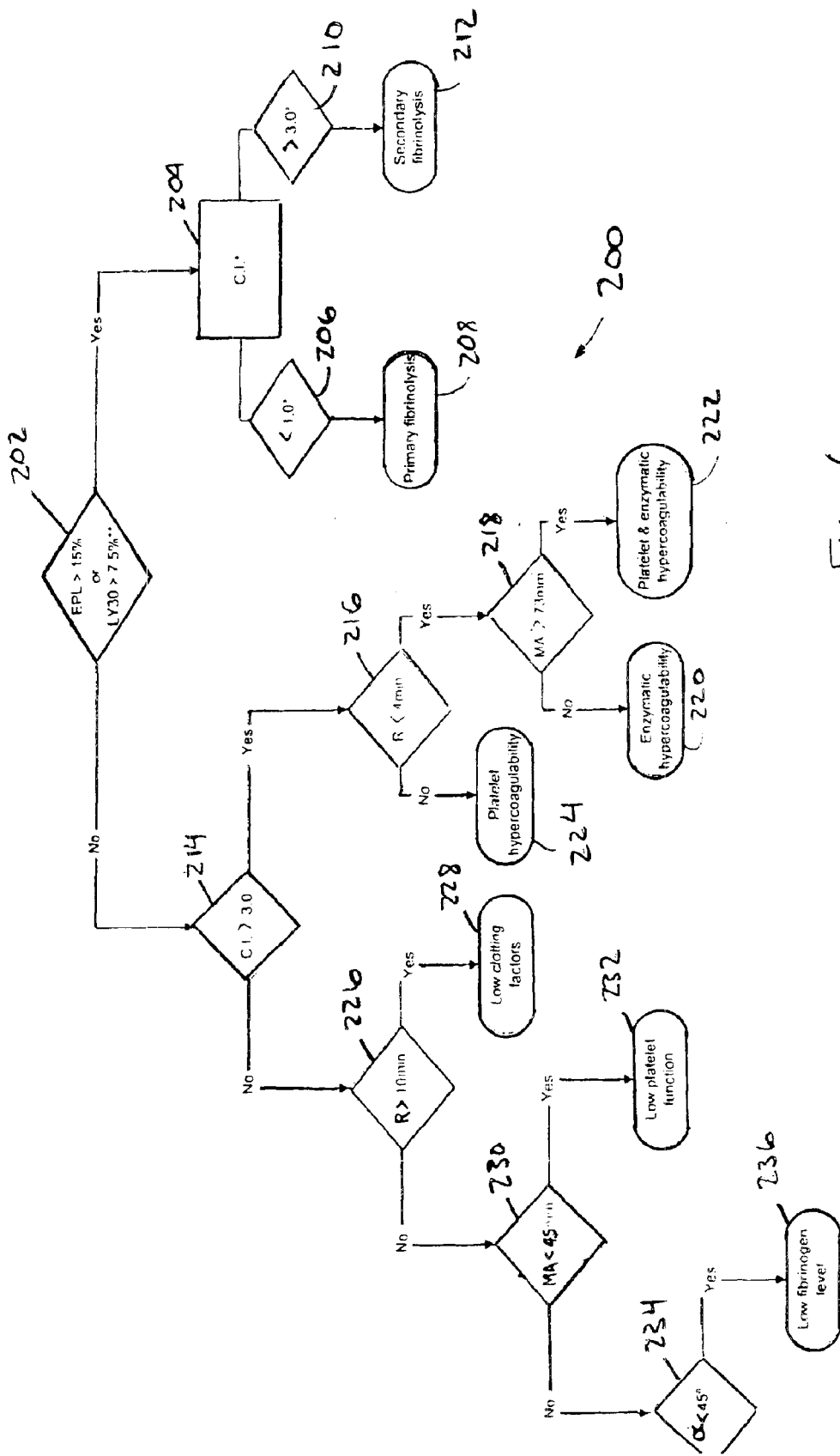
FIG. 6 is a flow chart illustrating a procedure for use with a hemostasis analyzer for guiding the management of patient hemostasis and blood therapy.

Referring to FIG. 5, a procedure 100 is outlined therein for hemostasis analyzer guided management of hemostasis, blood component usage and/or pharmaceutical therapy, and to FIG. 6 wherein a decision tree 200 is defined to assist interpretation of the results provided by the hemostasis analyzer. The following description of a particular sampling protocol associated with a cardiovascular procedure provides an illustration example that may be used to develop additional sampling protocol for particular medical/surgical procedures. It will be appreciated that sampling protocols will necessarily be developed for each particular procedure, and that the described sampling protocol for a cardiovascular procedure may not be appropriate in connection with other procedures, such as for example, trauma treatment or organ transplantation.

The sampling instructions in the procedure indicate that all blood samples are to be treated with low concentrations of kaolin. Kaolin is a reagent that acts as a control surface that activates Factor XII and platelets of a blood sample, which provides faster results without losing the sensitivity of measuring all phases of patient hemostasis or detecting low concentrations of heparin.

Another issue in evaluating hemostasis and coagulopathy in connection with the herein described cardiovascular procedure is heparin effect. The sampling outlined in the procedure may call for use of heparinase—an enzyme that breaks down the heparin—so that patient hemostasis in the presence and absence of heparin can be measured. Some samples are split and analyzed with heparinase and some are analyzed without heparinase. Using this technique, it is possible to see if there is any heparin effect, residual heparin, or line contamination. If the results from both samples are similar, for example, both R values are within normal limits, then heparin has been effectively reversed. If, using the TEG® hemostasis analyzer, R with heparinase is normal, but R without is elongated, then the heparin is not completely reversed.

Note that if the patient has not been treated with heparin as part of the cardiovascular procedure, coagulopathy should be evaluated based on the sample without heparinase. One of the advantages of TEG® hemostasis analysis is that samples can be run simulating in vivo conditions in the sample cup—and should. So, in the case where the patient is not on heparin, hemostasis assessment should be based on the sample without heparinase.

According to the exemplary cardiovascular sampling protocol 100 outlined in FIG. 4, samples are drawn at four time points:
Baseline on induction
At rewarming (about 36°)
Ten minutes post protamine
Post surgery.
Baseline Sample When the patient comes into the operating room a baseline sample is run as a starting point of the measuring stick for patient hemostasis and to establish whether the patient is hypercoagulable or has a tendency to bleed. This specimen is split into two aliquots, sample 1 and sample 2. One of the samples is analyzed using heparinase and one is analyzed without heparinase to check for heparin effect as well as for antithrombin deficiency. Conveniently, the TEG® hemostasis analysis system allows for the use of plain sample cups and pins (clear cups) and sample cups and pins treated with heparinase (blue cups).

Antithrombin deficiency is easily shown if the heparinase R and non-heparinase R are the same when heparin has been administered either to the patient or to the sample in the cup.

Antithrombin deficiency is typically treated with ATIII or fresh frozen plasma (FFP). If the patient is hypercoagulable, antifibrinolytic drugs are contraindicated unless the patient has been treated with platelet inhibitors or has the tendency to bleed, in which case Aprotinin (Trasylol) is suggested.

At Rewarming

A sample, sample 3, is drawn at rewarming of the patient—approximately 36°—and shows the maximum expression of any coagulopathy that has developed during the procedure. Sample 3 is another notch on the hemostasis measuring stick for two effects:

the effect of the trauma of surgery on the patient's hemostasis the net effect of extracorporeal surfaces on hemostasis at a time when the blood has been on the pump for the longest time.

Extra-corporeal devices, in general, reduce hypercoagulability, but in the case of off pump coronary artery bypass (OPCAB) the patient becomes more hypercoagulable. The results from sample 3 are typically used to determine which drug products are required (and are usually administered at this time), and which blood products should be ordered for administration later.

The MA value of sample 3 is typically 5 to 7 mm lower at this point than the post protamine sample, described below, and this should be taken into consideration when evaluating the results. This is particularly true if the value is borderline low and platelets, which may not be needed, are being considered.

Usually, if rewarming values are normal, patient hemostasis will continue to be normal post surgery. However, the patient should still be monitored for residual heparin effect (post protamine), surgical bleeding, or at a later time for hypercoagulability.

10 Minutes Post Protamine

At this point, the patient has been treated with protamine to neutralize the heparin. This is a split sample, samples 4 and 5, used to compare the R with and without heparinase as a check for residual heparin. If the R's are equal for both sample 4 and sample 5, the heparin has been effectively neutralized. If the R without heparinase is longer than with, there is residual heparin.

Samples 4 and 5 also show the importance of the baseline sample, since the degree of change from baseline is significant. Where the change between the baseline MA and the post protamine MA is great, that is, a baseline MA that is high and falls to the borderline transfusion trigger value, is a predictor of greater oozing or bleeding than where the difference is smaller, and should be considered for treatment accordingly.

If the sample post protamine shows coagulopathy, most likely it is consistent with what was already observed while the patient was on the bypass pump.

Post Surgery

After surgery—one hour in the intensive care unit (ICU)—the sample provides a wealth of information. Perhaps the most important is that it is a check if treatment so far was effective. It is also the point at which to evaluate the amount of chest tube drainage and heparin rebound. If there has been an increase in the hypercoagulability, consideration should be given to whether to anticoagulate or to order more testing, such as at 2 hour intervals.

If the hemostasis analysis results look normal, i.e., they do not indicate any coagulopathy, but the patient is bleeding, then there is likely no coagulopathy. It's most likely surgical bleeding. However, consideration should be given to von Willebrand's disease or acquired von Willebrand's factor (VWF) deficiency. In this case, the clot is fully functional, but it cannot adhere to the damaged vascular site, due to poor platelet-to-sub endothelial collagen bonding. Surgical bleeding can typically be differentiated from VWF deficiency by the greater rate of bleeding associated with surgical bleeding. However, because of the increased risk to the patient in misdiagnosing VWF deficiency as surgical bleeding, consider treating the patient with FFP or cryoprecipitate (cryo) (which carries VWF as part of Factor VIII) to confirm, or with desmopressin acetate (DDAVP) to stimulate the release of VWF by the endothelium. If the bleeding is diminished by treatment, VWF deficiency is indicated. If bleeding continues despite treatment, surgical bleeding is indicated, and the FFP or cryo is needed in any case for volume replacement.

When there is proline deficiency at the surgical site, surgical bleeding may be remedied clinically with continuous product transfusion, and this remedy should be considered before reexploration. If there are indications of large amounts of post-surgical bleeding at the site, reexploration may be required to remedy the problem.

Thus, according to one procedure in accordance with the invention, samples are drawn at multiple time points, and these samples may be treated with kaolin to achieve faster analysis results. Comparison of heparinase treated samples to non-treated samples evaluates degree of heparin effect, residual heparin effect, heparin rebound, and patient hemostasis in the presence of heparin. Following this sampling protocol gives a complete picture of the patient's hemostasis as it shifts from baseline through surgery and into the ICU. These samples, when evaluated against the decision tree 200 (FIG. 6), provide additional answers regarding treatment of developing coagulopathies or surgical bleeding. While the above-described sampling protocol is primarily adapted for use in connection with a cardiovascular procedure, the decision tree 200 has general applicability to the diagnosis and treatment of coagulopathies. The decision tree 200 may be implemented as a guide associated with the blood hemostasis analyzer. Conveniently, the decision tree 200 may be implemented as part of the control program 34 used by the computer 30 to control operation of the blood hemostasis analyzer. Alternatively, the blood hemostasis analyzer may include communication capability and may communicate with a remote computing device, such as a remotely located computer, a handheld computer and the like, via the Internet or other communication network using wired and/or wireless connections. An arrangement of a blood hemostasis analyzer to communicate with a remote computer that may be used is described in the aforementioned U.S. patent application Ser. No. 09/974,044 the disclosure of which is incorporated herein.

The decision tree 200 helps identify the coagulopathy and in the case of hyperfibrinolysis, can distinguish between primary and secondary fibrinolysis. In the case of hypercoagulability, it may be necessary to use a hemostasis analysis technique that can distinguish between platelet-induced vs. enzymatic hypercoagulability. The TEG hemostasis analysis system allows for making this distinction.

In applying hemostasis analysis results to the decision tree 200, the first evaluation is for hyperfibrinolysis. Using TEG hemostasis analysis, there is an indication of hyperfibrinolysis where LY30>7.5%. If LY30 isn't yet available, EPL—an estimate of lysis—may be used instead, with a value of >15% indicating fibrinolysis (202).

If the sample shows fibrinolysis next the coagulation index (CI) is evaluated (204). If the coagulation index is less than one, CI<1 (206), the patient is not hypercoagulable, and this is primary fibrinolysis (208). If the sample shows fibrinolysis and the coagulation index is greater than 3, CI>3 (210), indicating hypercoagulability, then it is secondary fibrinolysis (212)—it is secondary to the hypercoagulability. Making the determination of primary fibrinolysis then becomes easy—if it is not secondary fibrinolysis (212), it is primary fibrinolysis (206).

The D-dimer test is frequently used to diagnose fibrinolysis, but it gives an elevated result for both types of fibrinolysis, and this is extremely risky. It leads to a misdiagnosis, and the penalty to the patient of misdiagnosing secondary fibrinolysis as primary can be fatal. For example, suppose a mistaken diagnosis of secondary fibrinolysis is treated with antifibrinolytics such as Amicar. This treatment in effect blocks the pathway to break down the clot and therefore increases the probability of an ischemic event.

On the other hand, if a mistaken diagnosis of secondary fibrinolysis is treated with anticoagulants—making the patient bleed more—the penalty is not as great. Continued or increased bleeding can be neutralized with drugs, as in neutralizing heparin with protamine. Antifibrinolytic drugs such as Amicar may then be given to treat the primary fibrinolysis.

On the other branch of the decision tree 200, when LY30<7.5 (202) (no hyperfibrinolysis), evaluation is made first for hypercoagulability. A coagulation index greater than 3, CI>3 (214) indicates hypercoagulability. The next step is to decide between enzymatic and platelet hypercoagulability. If using the TEG® hemostasis analysis system a check of R is made. If R is short, for example less than 4 minutes (216), it's enzymatic (220). In addition, if R is short (216) and platelet function is high, MA is high, greater than 73 mm (218), it is due to high enzymatic reaction and high platelet activation (222). On the other hand, if R is normal and MA is high, hypercoagulability is due to high platelet function (224). Treatment with platelet inhibitors such as aspirin, ADP inhibitors such as Plavix, or GPIIb/IIIa inhibitors such as ReoPro, Integrilin, and Aggrastat is indicated.

When CI<3 (214)—not hypercoagulable—and R is elongated, greater than 10 minutes (226) the first priority is to normalize the R. This long R is due to low clotting factors (228) from coagulopathy or hemodilution resulting in a low rate of thrombin formation, which activates the platelets and cleaves the soluble fibrinogen into fibrin. The best treatment is FFP for clotting factors. If R is normal—no hypercoagulability—and MA is <45 mm (230) indicating low platelet function (232), typical treatment is with DDAVP or one unit of platelets. If MA<48 mm, platelets should be administered appropriately as described in connection with the treatment guide depicted in FIG. 7. If R and MA appear normal, but alpha is low $\alpha<45°$ (234), you can correct for low fibrinogen level (236) by treating with cryo, which not only contains high concentrations of fibrinogen, but also has high concentrations of factor VIII and factor XIII.

In some situations, R may be slightly elongated post protamine due to hemodilution. In such cases, the patient is usually not bleeding and no treatment is needed. If the hemostasis analysis results are normal but the patient is still oozing, that should gradually diminish.

The decision tree 200 arranges the evaluation criteria in a logical manner and is used to arrive, in a systematic way, at a coagulopathy diagnosis. All the hemostasis parameters are interdependent, and it is necessary to evaluate the parameters relative to each other, in addition to the patient's clinical status and bleeding state, to determine if a coagulopathy is present, which coagulopathy it is, and how to treat it. FIG. 7 illustrates a treatment guide 300 that may be part of the protocol to assist in this last step.

Referring to FIG. 7, the treatment guide 300 provides guidance and a treatment suggestion based on hemostasis analysis results. Knowing the part of the hemostasis process that is represented by each of the parameters leads to the hemostasis state of the sample, and, thus, knowing the magnitude of a parameter indicates the level of coagulopathy. Having identified this, then appropriate treatment in the right dosage becomes easier to determine.

As an illustration, using the decision tree, a R value over 10 mm indicates low clotting factors. The treatment guide 300 expands on that and indicates that R between 11 and 14 shows slightly low clotting factors and should be treated with 2 units of FFP, while R>14 indicates more severe shortage of clotting factors and should be treated with twice that—4 units of FFP.

Similarly, MA values less than 55 mm indicate low platelet function and three categories of MA are shown for increasing levels of platelet dysfunction, with corresponding increasing therapy. Slightly low levels can be treated with DDAVP, one unit of platelets, or nothing at all as it may be possible to simply wait for the patient's own platelets to recover.

The treatment guide 300 gives specific guidance in how to treat the coagulopathies that are already present or develop during and after surgery. The degree of coagulopathy can be evaluated by the magnitude of the hemostasis analysis values reported, and treatment determined and adjusted based on those values.

The decision tree 200 and treatment guide 300 may be further used to test potential treatment protocols prior to administering the treatment to a subject. The efficacy of a proposed treatment can be tested by adding the pharmaceutical or blood product to a blood sample in vitro. Prior in vitro evaluation of the treatment protocol can provide an indication of the efficacy on patient hemostasis in vivo. In this manner, hemostasis, blood product usage and pharmaceutical therapy is managed by first testing according to a sampling protocol, determining a coagulopathy based upon a decision tree and identifying a treatment in view of a treatment guide. The propose treatment may then by tested in vitro to confirm efficacy. It will be appreciated that a post treatment sampling and testing protocol.

Introduction of blood to artificial surface devices (ASD) such as cardiac bypass devices, artificial valves, dialysis, cardiac assist devices and cardiac replacement devices (total artificial heart devices) may lead to a number of hemostasis complications. Causes of thrombosis may include:

1. ASD-induced activation of the intrinsic/extrinsic pathway and the creation of the prothrombotic state. This results in the formation of thrombin and the formation of thrombotic deposits.

2. ASD-induced activation of platelets by agonists other than thrombin. Negatively-charged ASD surfaces or turbulent blood flow-induced shear stress that can cause binding of the activated platelets to the ASD. These activated platelets form and release additional agonists—thromboxane and ADP—thereby activating and aggregating other platelets in the blood stream. This is likely to be the primary cause of ASD thrombosis and is thus the basis for therapeutic measures described later.

3. Induction of hypersensitive platelets again due to exposure to the negatively charged ASD surface and/or turbulent blood flow plus the absence of the normal anti-platelet activity of the endothelial cell lining. These sensitized platelets may respond more easily and strongly to other sites of pre-existing or surgery-incurred vascular injury.

4. High fibrinogen level.

5. Antithrombin (AT) deficiency due to consumption of AT by thrombin.

6. Heparin-induced thrombocytopenia (HiT) due to the continuous circulation of heparinized blood through the vascular system.

The ASD may also lead to hemorrhage. Causes of hemorrhage may include:

1. Consumption of platelets and coagulation factors due to the activation of the hemostasis system.

2. Excess of anticoagulants.

3. Hyperfibrinolysis.

Figure 8:
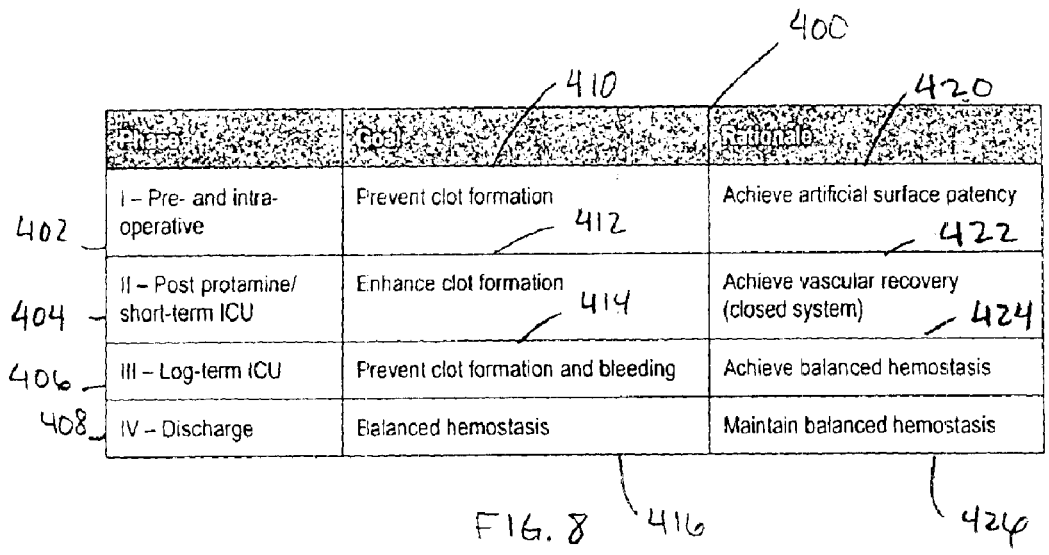
FIG. 8 is a table illustrating a phased monitoring protocol for ASD recipients.

Referring now to FIG. 8, there is depicted a table 400 illustrating a four phase protocol for monitoring hemostasis, particularly in connection with recipients of ASD. One of skill in the art will appreciate that the protocol illustrated in FIG. 8 and described in more detail in connection with FIGS. 9a–9d, has application generally in the monitoring and management of patient hemostasis. As shown in FIG. 8, the protocol is separated into four phases: pre- and intra-operative 402, post operative/short-term ICU 404, stabilizing/log-term ICU 406 and discharge/maintenance 408. Each phase has a corresponding treatment goal: clot formation prevention 410, clot formation enhancement 412, clot formation and bleeding prevention 414 and hemostasis balance 416 and a corresponding rational: achieve artificial surface patency 420, achieve vascular recovery (closed system) 422, achieve balanced hemostasis 424 and maintain balanced hemostasis 426.

Figure 9A:
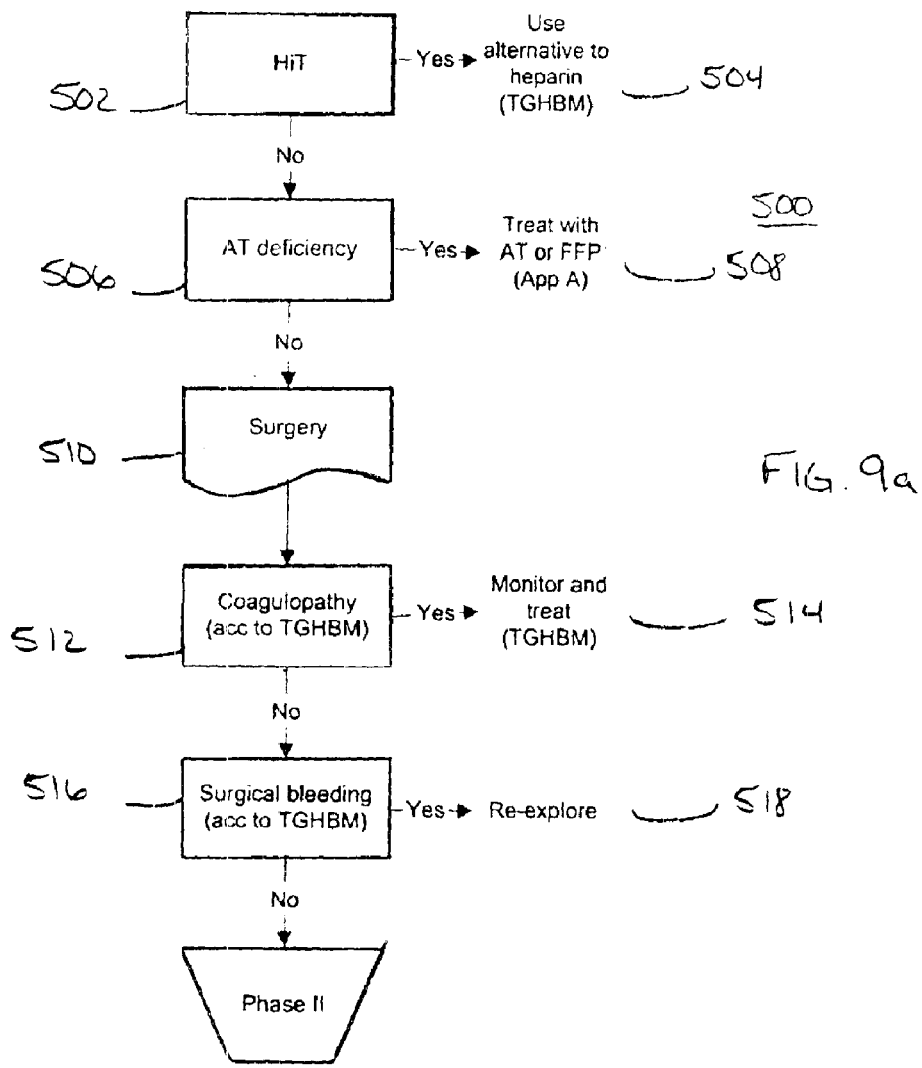

Referring now to FIG. 9a, Phase I, 402 is described in connection with the flow chart 500. The focus at Phase I 402, before and during surgery, is to prevent clot formation. The patient must be highly anticoagulated to prevent formation of thrombi and to achieve artificial surface patency. Phase I 402 begins pre-operatively and continues intra-operatively. Monitoring during this phase may consist of the following steps:

At baseline, check for HiT, step 502. In the presence of HiT, other thrombin inhibitors such as hirudin or angiomax should be considered, step 504. At baseline, check for AT deficiency step 506. In the presence of AT deficiency, treat with AT with the dosing regimen recommended by the manufacturer or transfuse FFP as necessary to achieve the targeted ACT values, step 508. The patient is then highly anticoagulated in preparation for the surgery, 510. At steps 512 and 514, the patient may be monitored and treated according to the decision tree 200 and treatment guide 300.

Heparin is an indirect anticoagulant. It acts mainly by stimulating the natural anticoagulant antithrombin (AT) to inhibit thrombin. When AT is below a certain plasma level, the anticoagulating effect of heparin is diminished, and the patient will be resistant to heparin. A hemostasis analyzer may be used to determine AT deficiency according to the following protocol.

For a patient on heparin:

1. Draw a blood sample and test separate portions of the sample with and without heparinase. If the fibrin formation latency period, e.g., the R parameter provided by the TEG® hemostasis analysis device, is much shorter for the with heparinase sample, there is no AT deficiency.

2. If the fibrin formation latency period is not much shorter in the first test, separate portions of the sample are tested one with and one without heparinase and both with antithrombin. If the fibrin formation latency period is much shorter for the sample tested with heparinase than for the sample tested without heparinase, the AT deficiency is indicated.

For a patient not on heparin:

1. Draw a blood sample. Test separate portions of the sample each with heparin add and one with and one without heparinase. If the fibrin formation latency period, e.g., the R parameter provided by the TEG® hemostasis analysis device, is much shorter for the with heparinase sample, there is no AT deficiency.

2. If the fibrin formation latency period is not much shorter in the first test, separate portions of the sample are tested, one with and one without heparinase and both with heparin and antithrombin. If the fibrin formation latency period is much shorter for the sample tested with heparinase than for the sample tested without heparinase, the AT deficiency is indicated.

The focus of Phase II 404 is to enhance clot formation and is described in connection with the flowchart 600 of FIG. 9b. At step 602 monitoring and treatment according to the decision tree 200 and treatment guide 300 is continued. If coagulopathy is detected, the patient is treated accordingly, step 604. If surgical bleeding is found to exist, step 606, surgery is indicated, step 608, and Phase I is repeated.

Phase II continues until the patient achieves a restoration of normal hemostasis and recovery of vascular integrity (closed system). This phase may continue one to two days in the ICU with close monitoring every 3–4 hours, step 610. During Phase II, the possibility of gastrointestinal (GI) bleeding, internal bleeding in the retro-peritoneum, or other bleeding diathesis must be checked. During Phase II, the need for additional testing such as CT may be considered.

Special attention should be given if the patient is hypothermic post surgery. At step 612, the effects of hypothermia are determined by testing a sample of the patient's blood at the patient's body temperature and a second sample at a temperature of 37° C. The difference in patient hemostasis would be attributed to the effects of hypothermia, and the patient is warmed, step 614. If the hypothermic patient is bleeding but his hemostasis in the 37° C. sample is normal, this is an indication that, as the patient warms up, the bleeding may stop. On the other hand, if the 37° C. sample shows coagulopathy and the patient is bleeding, then the coagulopathy can be treated according to the decision tree 200 and treatment guide 300 until the 37° C. sample is normalized. If the hypothermic patient still continues to bleed, this bleeding can be attributed to the hypothermia.

At step 616, chest tube drainage is checked. If bleeding is under control and chest tube drainage (CTD) is diminishing toward 30 cc/hr, vascular recovery is being achieved and the patient is ready for Phase II. Otherwise, the patient is treated in connection with the decision tree 200 and treatment guide 300 until bleeding is brought under control.

Phase III, illustrated in the flowchart 700 shown in FIG. 9c, is triggered when CTD approaches 30 cc/hr, which indicates vascular recovery and-achieving a closed system. The focus in Phase III shifts from enhancing clot formation to anticoagulation and the prevention of ischemic events that may be caused by continuous exposure of the blood to ASD surface and/or the presence of sepsis. As mentioned above, ischemic events are the result of enzymatic activation of patient hemostasis resulting in the formation of fibrin-platelet thrombi (red clots) or platelet activation, resulting in the formation of platelet thrombi (white clots). To prevent these ischemic events, an anticoagulation regimen needs to be initiated and closely monitored to achieve a delicate balance of the anticoagulated state.

Patient anticoagulation without hemorrhage can only be achieved by successfully achieving vascular recovery in Phase II. Only then can anticoagulation begin, step 702. Since it is now a closed vascular system, it is permissible to err slightly on the side of anticoagulation to prevent ischemic events without causing hemorrhage.

To achieve anticoagulation with the appropriate balance between hemorrhage and thrombosis, both enzymatic and platelet anticoagulation must be considered. A protocol for achieving this balance is described in connection with FIG. 10.

Anticoagulation is accomplished in two steps, first in achieving recommended value ranges for hemostasis analysis parameters, e.g., TEG® R and MA platelet inhibition parameters, which reflect a balanced hemostatic state specific to that patient; and second in maintaining the balanced state. Careful close and continued monitoring of hemostasis parameters along with other clinical parameters is important in achieving and maintaining a balanced state of individualized patient hemostasis.

The starting point of the enzymatic anticoagulation regimen is to achieve an $R_K$ parameter between 12.0 and 16.0 min, which is 1.5 to 2.0 times the normal range, ACT greater than 180 sec, and aPTT greater than 50 sec, where $R_K$ is the TEG® R using a sample treated with kaolin and without heparinase. An anticoagulant, such as heparin should be started at a suitable dose, such as 5 USP/kg/hr for heparin, and increased if necessary to reach the recommended $R_K$. If the recommended $R_K$ is achieved but ACT<180 sec or aPTT<50 sec. heparin dosing is continued to increase the recommended $R_K$ until all enzymatic anticoagulation conditions are satisfied.

FIG. 10 outlines a suggested platelet anticoagulation treatment regimen based upon the use of either aspirin or Plavix®. Aspirin is administered and the clot strength is measured, e.g., the TEG® $MA_{Kh}$ parameter, to determine resistance to aspirin therapy. Depending on the patient's resistance to aspirin, as indicated by the clot strength parameter, Plavix® may be administered.

Once the target fibrin formation latency time, $R_{KH}$, clot strength, $MA_{KH}$, and platelet inhibited clot strength, $MA_{PI}$, values described in FIG. 10 have been achieved, close monitoring may be continued every six hours, and, if necessary, the dosage of heparin (or alternative anticoagulant in the presence of HiT, steps 706 and 708) and platelet inhibitors adjusted to achieve CTD between 30 cc/hr and 60 cc/hr. with no clot formation. The parameter values that keep the patient in a balanced hemostatic state are specific to that patient and the ASD. Gradually there is a shift to monitoring the patient every twelve hours and subsequently every twenty-four hours.

In certain instances, it may be useful to run one or more of the following laboratory tests periodically in addition to hemostasis analysis device, e.g., TEG® device, monitoring until a hemostasis balance is achieved: PT, aPTT, INR, fibrinogen level, hemoglobin, hematocrit, hemolysis, white cell count, platelet count, and ACT. A high fibrinogen level may indicate a need for drugs like pentoxifylline (Trental). A high platelet number may indicate a need for drugs like anagrelide hydrochloride (Agrylin®) to reduce the production of platelets by the bone marrow. Note that high platelet counts by Coulter counting could be due to red blood cell fragmentation caused by the ASD, and this should be ruled out by microscopic examination of blood smears.

Furthermore, due to the continuous circulation of heparinized blood through the vascular system, heparin-induced antibodies may form, resulting in the onset of HiT. Therefore, a HiT test, step 704, should be conducted again upon any significant reduction in platelet count. Confirming the presence of HiT indicates that heparin should be stopped and Coumadin therapy begun immediately together with another anticoagulant such as hirudin for a day or so until the effects of Coumadin have been shown, step 706.

During this phase of heparin therapy, one should also be aware of possible AT consumption and a test for AT deficiency, such as described above, should be performed, step 708. If AT deficiency is indicated, then treatment with antithrombin or FFP should be considered, step 710. The recipient is also be monitored to verify he is not prothrombotic, step 712. If thrombosis is indicated, anticoagulation therapy may be initiated, such as described above, step 714. Otherwise, hemostasis balance, with a potential bias toward anticoagulation, is achieved, step 716, and the recipient moves to phase IV.

Phase IV, described in connection with the flowchart 800 of FIG. 9d, focuses on maintaining a balanced hemostasis. The success of Phase IV is dependent on achieving the patient's own balance in Phase III. Once this is achieved, anticoagulation should be changed from heparin to another suitable compound, such as Coumadin, step 802, at a suitable dose. The recipient is then monitored to achieve an appropriate individualized R value, step 804. If the R value is not within a desired range for the recipient, then the dosage of the anticoagulation compound is adjusted, step 806. Monitoring is continued to ensure the patient does not become prothrombotic, step 808. If a protrhombotic state is indicated, the hemostasis balance is reestablished by anticoagulation therapy, step 810. Otherwise, hemostasis balance is maintained, step 812.

During Phase IV, patient hemostasis may be monitored every 24 hours and monitoring may be decreased weekly by increments of 24 hours. The patient should be prepared for discharge, step 814, and after discharge monitoring may be continued once a week, diminishing gradually to once a month.

The invention has been described in terms of several preferred embodiments. One of skill in the art will appreciate that the invention may be otherwise embodied without departing from its fair scope, which is set forth in the subjoined claims.

We claim:

1. A method for monitoring hemostasis in a connection with a recipient of an artificial surface device, the method comprising the steps of:

monitoring hemostasis of the recipient in a pre- and intra-operative phase relative to preventing clot formation to achieve artificial surface patency;

monitoring hemostasis of the recipient in a post operative phase relative to bringing about clot formation to achieve vascular recovery;

monitoring hemostasis of the recipient in a stabilizing intensive care phase relative to balancing hemostasis toward an anti-coagulation bias; and monitoring hemostasis of the recipient in a maintenance phase to maintain balanced hemostasis.

2. The method of claim 1, wherein the step of monitoring hemostasis in a pre- and intra-operative phase comprises determining an anti-thrombin deficiency of the recipient.

3. The method of claim 1, wherein the step of monitoring hemostasis in a pre- and intra-operative phase comprises determining an intra-operative coagulopathy of the recipient.

4. The method of claim 1, wherein the step of monitoring hemostasis in a pre- and intra-operative phase comprises determining a surgical bleeding condition of the recipient.

5. The method of claim 1, wherein the step of monitoring hemostasis of the recipient in a post operative phase comprises determining a post protamine coagulopathy of the recipient.

6. The method of claim 1, wherein the step of monitoring hemostasis of the recipient in a post operative phase comprises determining a surgical bleeding condition of the recipient.

7. The method of claim 1, wherein the step of monitoring hemostasis of the recipient in a post operative phase comprises determining a hypothermia condition of the recipient.

8. The method of claim 1, wherein the step of monitoring hemostasis of the recipient in a post operative phase comprises determining a chest tube draining condition of the recipient.

9. The method of claim 1, wherein the step of monitoring hemostasis of the recipient in a stabilizing intensive care phase comprises determining a heparin-induced thrombocytopenia condition of the recipient.

10. The method of claim 1, wherein the step of monitoring hemostasis of the recipient in a stabilizing intensive care phase comprises determining an anti-thrombin condition of the recipient.

11. The method of claim 1, wherein the step of monitoring hemostasis of the recipient in a stabilizing intensive care phase comprises determining a prothrombotic condition of the recipient.

12. The method of claim 1, wherein the step of monitoring hemostasis of the recipient in a maintenance phase comprises determining a fibrin formation latency period (R) of the recipient.

13. The method of claim 1, wherein the step of monitoring hemostasis of the recipient in a maintenance phase comprises determining a prothombotic condition of the recipient.

14. An apparatus for monitoring hemostasis in a connection with a recipient of an artificial surface device, the apparatus comprising:

means for monitoring hemostasis of the recipient in a pre- and intra-operative phase relative to preventing clot formation to achieve artificial surface patency;

means for monitoring hemostasis of the recipient in a post operative phase relative to bringing about clot formation to achieve vascular recovery;

means for monitoring hemostasis of the recipient in a stabilizing intensive care phase relative to balancing hemostasis toward an anti-coagulation bias; and means for monitoring hemostasis of the recipient in a maintenance phase to maintain balanced hemostasis.

15. The apparatus of claim 14, wherein each of the means for monitoring comprises a hemostasis analysis device.

16. The apparatus of claim 15, wherein the hemostasis analysis device comprises a processor and a memory coupled to a testing station, the processor being responsive to a control program stored within the memory for directing operation of the testing station and to obtain and analyze data from the testing station to provide at least one hemostasis parameter.

* * * * *

UNITED STATES PATENT AND TRADEMARK OFFICE
CERTIFICATE OF CORRECTION

PATENT NO. : 6,890,299 B2
DATED : May 10, 2005
INVENTOR(S) : Eli Cohen et al.

It is certified that error appears in the above-identified patent and that said Letters Patent is hereby corrected as shown below:

Column 14,
Line 7, please delete "prothombotic" and insert -- prothrombotic --.

Signed and Sealed this

Twenty-third Day of August, 2005

JON W. DUDAS
*Director of the United States Patent and Trademark Office*